US008753320B2

(12) United States Patent
Miller

(10) Patent No.: US 8,753,320 B2
(45) Date of Patent: Jun. 17, 2014

(54) METHOD TO SECURE AN ELASTIC COMPONENT IN A VALVE

(75) Inventor: Stephen C. Miller, Queensbury, NY (US)

(73) Assignee: Navilyst Medical, Inc., Marlborough, MA (US)

( * ) Notice: Subject to any disclaimer, the term of this patent is extended or adjusted under 35 U.S.C. 154(b) by 37 days.

(21) Appl. No.: 13/176,054

(22) Filed: Jul. 5, 2011

(65) Prior Publication Data
US 2011/0264054 A1 Oct. 27, 2011

Related U.S. Application Data

(63) Continuation of application No. 12/501,809, filed on Jul. 13, 2009, now Pat. No. 8,007,468.

(51) Int. Cl.
*A61M 5/14* (2006.01)

(52) U.S. Cl.
USPC ............... 604/256; 251/149; 604/167.04

(58) Field of Classification Search
USPC ........... 604/167.04, 247, 256; 251/149, 335.1
See application file for complete search history.

(56) References Cited

U.S. PATENT DOCUMENTS

| 2,446,571 | A | 3/1944 | Browne |
| 2,720,881 | A | 10/1955 | Weaver et al. |
| 2,755,060 | A | 7/1956 | Twyman |
| 3,113,586 | A | 12/1963 | Edmark, Jr. |
| 3,159,175 | A | 12/1964 | MacMillan |
| 3,159,176 | A | 12/1964 | Russell et al. |
| 3,477,438 | A | 11/1969 | Allen et al. |
| 3,514,438 | A | 5/1970 | Nelsen et al. |
| 3,525,357 | A | 8/1970 | Koreski |
| 3,621,557 | A | 11/1971 | Cushman et al. |
| 3,669,323 | A | 6/1972 | Harker et al. |
| 3,673,612 | A | 7/1972 | Merrill et al. |
| 3,674,183 | A | 7/1972 | Venable et al. |
| 3,710,942 | A | 1/1973 | Rosenberg |
| 3,788,327 | A | 1/1974 | Donowitz et al. |
| 3,811,466 | A | 5/1974 | Ohringer |
| 3,941,149 | A | 3/1976 | Mittleman |
| 3,955,594 | A | 5/1976 | Snow |
| 4,072,146 | A | 2/1978 | Howes |
| 4,142,525 | A | 3/1979 | Binard et al. |

(Continued)

FOREIGN PATENT DOCUMENTS

| DE | 20208420 | 10/2002 |
| EP | 0128625 | 12/1984 |

(Continued)

OTHER PUBLICATIONS

International Search Report and Written Opinion mailed Sep. 3, 2010 for International Application No. PCT/US2010/041698 (10 pages).

(Continued)

*Primary Examiner* — Kevin C Sirmons
*Assistant Examiner* — Deanna K Hall
(74) *Attorney, Agent, or Firm* — Ryan D. Artis

(57) ABSTRACT

An apparatus for controlling fluid flow to provide long-term access to the vascular system, and methods of making the same, are disclosed. Exemplary embodiments of the present invention describe a wedge or other similarly shaped geometrical feature for fixing an elastic component and controlling an internal stress of the elastic component.

11 Claims, 2 Drawing Sheets

(56) References Cited

U.S. PATENT DOCUMENTS

| | | | |
|---|---|---|---|
| 4,143,853 | A | 3/1979 | Abramson |
| 4,244,379 | A | 1/1981 | Smith |
| 4,387,879 | A | 6/1983 | Tauschinski |
| 4,405,316 | A | 9/1983 | Mittleman |
| 4,434,810 | A | 3/1984 | Atkinson |
| 4,447,237 | A | 5/1984 | Frisch et al. |
| 4,468,224 | A | 8/1984 | Enzmann et al. |
| 4,502,502 | A | 3/1985 | Krug |
| 4,524,805 | A | 6/1985 | Hoffman |
| 4,543,087 | A | 9/1985 | Sommercorn et al. |
| 4,552,553 | A | 11/1985 | Schulte et al. |
| 4,610,665 | A | 9/1986 | Matsumoto et al. |
| 4,616,768 | A | 10/1986 | Flier |
| 4,646,945 | A | 3/1987 | Steiner et al. |
| 4,673,393 | A | 6/1987 | Suzuki et al. |
| 4,681,572 | A | 7/1987 | Tokarz et al. |
| 4,692,146 | A | 9/1987 | Hilger |
| 4,722,725 | A | 2/1988 | Sawyer et al. |
| 4,790,832 | A | 12/1988 | Lopez |
| 4,798,594 | A | 1/1989 | Hillstead |
| 4,801,297 | A | 1/1989 | Mueller |
| 4,908,028 | A | 3/1990 | Colon et al. |
| 4,944,726 | A | 7/1990 | Hilal et al. |
| 4,946,448 | A | 8/1990 | Richmond |
| 4,960,412 | A | 10/1990 | Fink |
| 5,000,745 | A | 3/1991 | Guest et al. |
| 5,009,391 | A | 4/1991 | Steigerwald |
| 5,030,210 | A | 7/1991 | Alchas et al. |
| 5,084,015 | A | 1/1992 | Moriuchi |
| 5,098,405 | A | 3/1992 | Peterson et al. |
| 5,125,893 | A | 6/1992 | Dryden |
| 5,147,332 | A | 9/1992 | Moorehead |
| 5,149,327 | A | 9/1992 | Oshiyama |
| 5,167,638 | A | 12/1992 | Felix et al. |
| 5,169,393 | A | 12/1992 | Moorehead et al. |
| 5,176,652 | A | 1/1993 | Littrell |
| 5,176,662 | A | 1/1993 | Bartholomew et al. |
| 5,201,722 | A | 4/1993 | Moorehead et al. |
| 5,205,834 | A | 4/1993 | Moorehead et al. |
| 5,249,598 | A | 10/1993 | Schmidt |
| 5,254,086 | A | 10/1993 | Palmer et al. |
| 5,324,274 | A | 6/1994 | Martin |
| 5,330,424 | A | 7/1994 | Palmer et al. |
| 5,336,203 | A | 8/1994 | Goldhardt et al. |
| 5,360,407 | A | 11/1994 | Leonard et al. |
| 5,370,624 | A | 12/1994 | Edwards et al. |
| 5,395,352 | A | 3/1995 | Penny |
| 5,396,925 | A | 3/1995 | Poli et al. |
| 5,399,168 | A | 3/1995 | Wadsworth et al. |
| 5,401,255 | A | 3/1995 | Sutherland et al. |
| D357,735 | S | 4/1995 | McPhee |
| 5,405,340 | A | 4/1995 | Fageol et al. |
| 5,411,491 | A | 5/1995 | Goldhardt et al. |
| 5,453,097 | A | 9/1995 | Paradis |
| 5,454,784 | A | 10/1995 | Atkinson et al. |
| 5,469,805 | A | 11/1995 | Gibbs et al. |
| 5,470,305 | A | 11/1995 | Arnett et al. |
| 5,484,420 | A | 1/1996 | Russo |
| 5,542,923 | A | 8/1996 | Ensminger et al. |
| 5,545,150 | A | 8/1996 | Danks et al. |
| 5,554,136 | A | 9/1996 | Luther |
| 5,562,618 | A | 10/1996 | Cai et al. |
| 5,571,093 | A | 11/1996 | Cruz et al. |
| 5,575,769 | A | 11/1996 | Vaillancourt et al. |
| 5,624,395 | A | 4/1997 | Mikhail et al. |
| 5,637,099 | A | 6/1997 | Durdin et al. |
| 5,667,500 | A | 9/1997 | Palmer et al. |
| 5,707,357 | A | 1/1998 | Mikhail et al. |
| 5,743,873 | A | 4/1998 | Cai et al. |
| 5,743,884 | A | 4/1998 | Hasson et al. |
| 5,743,894 | A | 4/1998 | Swisher |
| 5,752,938 | A | 5/1998 | Flatland et al. |
| 5,803,078 | A | 9/1998 | Brauner |
| 5,807,349 | A | 9/1998 | Person et al. |
| 5,810,789 | A | 9/1998 | Powers et al. |
| 5,843,044 | A | 12/1998 | Moorehead |
| 5,853,397 | A | 12/1998 | Shemesh et al. |
| 5,865,308 | A | 2/1999 | Qin et al. |
| 5,944,698 | A | 8/1999 | Fischer et al. |
| 5,984,902 | A | 11/1999 | Moorehead |
| 5,989,233 | A | 11/1999 | Yoon |
| 6,033,393 | A | 3/2000 | Balbierz et al. |
| 6,045,734 | A | 4/2000 | Luther et al. |
| 6,050,934 | A | 4/2000 | Mikhail et al. |
| 6,056,717 | A | 5/2000 | Finch et al. |
| 6,062,244 | A | 5/2000 | Arkans |
| 6,092,551 | A | 7/2000 | Bennett |
| 6,099,505 | A | 8/2000 | Ryan et al. |
| 6,120,483 | A | 9/2000 | Davey et al. |
| 6,152,909 | A | 11/2000 | Bagaoisan et al. |
| 6,210,366 | B1 | 4/2001 | Sanfilippo |
| 6,227,200 | B1 | 5/2001 | Crump et al. |
| 6,270,489 | B1 | 8/2001 | Wise et al. |
| 6,306,124 | B1 | 10/2001 | Jones et al. |
| 6,364,861 | B1 | 4/2002 | Feith et al. |
| 6,364,867 | B2 | 4/2002 | Wise et al. |
| 6,375,637 | B1 | 4/2002 | Campbell et al. |
| 6,436,077 | B1 | 8/2002 | Davey et al. |
| 6,442,415 | B1 | 8/2002 | Bis et al. |
| 6,446,671 | B2 | 9/2002 | Armenia et al. |
| 6,508,791 | B1 | 1/2003 | Guerrero |
| 6,551,270 | B1 | 4/2003 | Bimbo et al. |
| 6,610,031 | B1 | 8/2003 | Chin |
| 6,726,063 | B2 | 4/2004 | Stull et al. |
| 6,786,884 | B1 | 9/2004 | DeCant et al. |
| 6,874,999 | B2 | 4/2005 | Dai et al. |
| 6,953,450 | B2 | 10/2005 | Baldwin et al. |
| 6,994,314 | B2 | 2/2006 | Garnier et al. |
| 7,081,106 | B1 | 7/2006 | Guo et al. |
| 7,252,652 | B2 | 8/2007 | Moorehead et al. |
| 7,291,133 | B1 | 11/2007 | Kindler et al. |
| 7,316,655 | B2 | 1/2008 | Garibotto et al. |
| 7,435,236 | B2 | 10/2008 | Weaver et al. |
| 7,601,141 | B2 | 10/2009 | Dikeman et al. |
| 7,637,893 | B2 | 12/2009 | Christensen et al. |
| 7,758,541 | B2 | 7/2010 | Wallace et al. |
| 8,257,321 | B2 * | 9/2012 | Lareau et al. .................. 604/247 |
| 2001/0023333 | A1 | 9/2001 | Wisse et al. |
| 2001/0037079 | A1 | 11/2001 | Burbank et al. |
| 2002/0010425 | A1 | 1/2002 | Guo et al. |
| 2002/0016584 | A1 | 2/2002 | Wise et al. |
| 2002/0121530 | A1 | 9/2002 | Socier |
| 2002/0165492 | A1 | 11/2002 | Davey et al. |
| 2002/0193752 | A1 | 12/2002 | Lynn |
| 2003/0122095 | A1 | 7/2003 | Wilson et al. |
| 2004/0034324 | A1 | 2/2004 | Seese et al. |
| 2004/0064128 | A1 | 4/2004 | Raijman et al. |
| 2004/0102738 | A1 | 5/2004 | Dikeman |
| 2004/0108479 | A1 | 6/2004 | Garnier et al. |
| 2004/0186444 | A1 | 9/2004 | Daly et al. |
| 2004/0193119 | A1 | 9/2004 | Canaud et al. |
| 2004/0210194 | A1 | 10/2004 | Bonnette et al. |
| 2004/0267185 | A1 | 12/2004 | Weaver et al. |
| 2005/0010176 | A1 | 1/2005 | Dikeman et al. |
| 2005/0027261 | A1 | 2/2005 | Weaver et al. |
| 2005/0043703 | A1 | 2/2005 | Nordgren |
| 2005/0049555 | A1 | 3/2005 | Moorehead et al. |
| 2005/0149116 | A1 | 7/2005 | Edwards et al. |
| 2005/0171490 | A1 | 8/2005 | Weaver et al. |
| 2005/0171510 | A1 | 8/2005 | DiCarlo et al. |
| 2005/0283122 | A1 | 12/2005 | Nordgren |
| 2006/0129092 | A1 | 6/2006 | Hanlon et al. |
| 2006/0135949 | A1 | 6/2006 | Rome et al. |
| 2006/0149211 | A1 | 7/2006 | Simpson et al. |
| 2007/0161940 | A1 | 7/2007 | Blanchard et al. |
| 2007/0161970 | A1 | 7/2007 | Spohn et al. |
| 2007/0276313 | A1 | 11/2007 | Moorehead et al. |
| 2008/0108956 | A1 * | 5/2008 | Lynn et al. .................... 604/256 |
| 2009/0292252 | A1 | 11/2009 | Lareau et al. |

FOREIGN PATENT DOCUMENTS

| | | |
|---|---|---|
| EP | 0337617 | 10/1989 |
| EP | 0930082 | 7/1999 |

(56) References Cited

FOREIGN PATENT DOCUMENTS

| | | |
|---|---|---|
| EP | 1016431 | 7/2000 |
| FR | 2508008 | 12/1982 |
| FR | 2718969 | 10/1995 |
| GB | 966137 | 8/1964 |
| GB | 2102398 | 2/1983 |
| JP | 59133877 | 8/1984 |
| JP | 63255057 | 10/1988 |
| JP | 9038197 | 2/1997 |
| WO | WO-89/02764 | 4/1989 |
| WO | WO-91/12838 | 9/1991 |
| WO | WO-92/06732 | 4/1992 |
| WO | WO-95/16480 | 6/1995 |
| WO | WO-96/17190 | 6/1996 |
| WO | WO-96/23158 | 8/1996 |
| WO | WO-96/41649 | 12/1996 |
| WO | WO-97/23255 | 7/1997 |
| WO | WO-97/26931 | 7/1997 |
| WO | WO-98/22178 | 5/1998 |
| WO | WO-99/42166 | 8/1999 |
| WO | WO-00/06230 | 2/2000 |
| WO | WO-00/44419 | 8/2000 |
| WO | WO-01/74434 | 10/2001 |
| WO | WO-03/084832 | 10/2003 |
| WO | WO-2005/023355 | 3/2005 |
| WO | WO-2008/089985 | 7/2008 |

OTHER PUBLICATIONS

Asch, "Venous access: options, approaches and issues," Can Assoc. Radiol J., vol. 52, No. 3 pp. 153-164 (2001).
Herts et al., "Power injection of contrast media using central venous catheters: feasibility, safety, and efficacy," AJR Am. J. Roentgenol., vol. 176, No. 2, pp. 447-453 (2001).
Roth et al., "Influence of radiographic contrast media viscosity to flow through coronary angiographic catheters," Cathet. Cardiovasc. Diagn., vol. 22, No. 4, pp. 290-294 (1991).
Carlson et al., "Safety considerations in the power injection of contrast media via central venous catheters during computered tomogrphic examinations," Invest. Radiol., vol. 27, No. 5, p. 337-340 (1992).
Kaste et al., "Safe use of powr injectors with central and peripheral venous access devices for pediatrict CT," Pediatr. Radiol., vol. 26, No. 8, pp. 449-501 (1996).
Herts et al., "Power injection of intravenous contrast material through central venous catheters for CT: in vitro evaluation," Radiology, vol. 200, No. 3, pp. 731-735 (1996).
Rivitz et al., "Power injection of peripherally inserted central catheters," J. Vasc. Interv. Radiol., vol. 8, No. 5, pp. 857-863 (1997).
Rogalla et al., Safe and easy power injection of contrast material through a central line, Eur. Radiol., vol. 8, No. 1, pp. 148-149 (1998).
Williamson et al., "Assessing the adequacy of peripherally inserted central catheters for power injection of intravenous contrast agents for CT," J. Comput. Assist. Tomogr., vol. 25, No. 6, pp. 932-937 (2001).
Chahous et al., "Randomized comparison of coronary angiography using 4F catheters: 4F manual versus 'Acisted' power injection technique," Catheter Cardiovasc. Interv., vol. 53, No. 2, pp. 221-224 (2001).
Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).
Saito et al., "Diagnostic brachial coronary arteriography using a power-assisted injector and 4 French catheters with new shamps," J. Invasive Cardiol., vol. 9, No. 7, pp. 461-468 (1997).

\* cited by examiner

METHOD TO SECURE AN ELASTIC COMPONENT IN A VALVE

CROSS-REFERENCE TO PRIOR APPLICATIONS

This application is a continuation application of U.S. patent application Ser. No. 12/501,809 filed Jul. 12, 2009.

BACKGROUND

Pressure activated safety valves have been incorporated into medical devices such as peripherally inserted central catheters (PICCs), ports, dialysis catheters and tunneled central catheters which provide long term access to the vascular system, etc. These valves generally include an elastic component that controls flow and/or pressure through the device to prevent flow therethrough when the device is not in use. The elastic component may be a slitted, flexible membrane extending across a lumen generally constructed so that, when subjected to a fluid pressure of at least a threshold magnitude, edges of the slit separate from one another to permit flow through the lumen. When the pressure applied to the membrane drops below the threshold level, the slit reseals to prevent leakage from or into the device. It is desirable to keep the flexible disk in place during high pressure and/or flow while maintaining the desired flow control characteristics of the membrane.

SUMMARY OF THE INVENTION

The present invention is directed to a valve comprising a flexible member including a slit formed on a central portion thereof and a first housing defining a first lumen extending therethrough, the first housing including a first contacting surface adapted, when the slit of the flexible member is aligned with the first lumen, to contact a first side of the flexible member the first housing defining a relief area extending about a perimeter of the first contacting surface radially outside the central portion relative to a longitudinal axis of the first lumen in combination with a second housing adapted to mate with the first housing with a second lumen defined by the second housing aligned with the first lumen and separated therefrom by the flexible member, the second housing including a second contacting surface which, when the first and second housings are mated to one another in an operative configuration with the flexible member pinched therebetween, contacts a second side of the flexible member opposite the first side thereof along the longitudinal axis, a radially outer portion of the second contacting surface including a protrusion aligning with and extending into the relief area when the first and second housings are mated in the operative configuration, the protrusion bending a peripheral portion of the flexible member about a radially outer edge of the first contacting surface into the relief area to maintain the flexible member at a desired position separating the first and second lumens so that, when subject to a fluid pressure of at least a predetermined magnitude, the slit of the flexible member opens to permit fluid transfer between the first and second lumens and, when subject to a fluid pressure less than the predetermined magnitude, the slit of the flexible member remains closed preventing fluid transfer between the first and second lumens.

DETAILED DESCRIPTION

Figure 1:
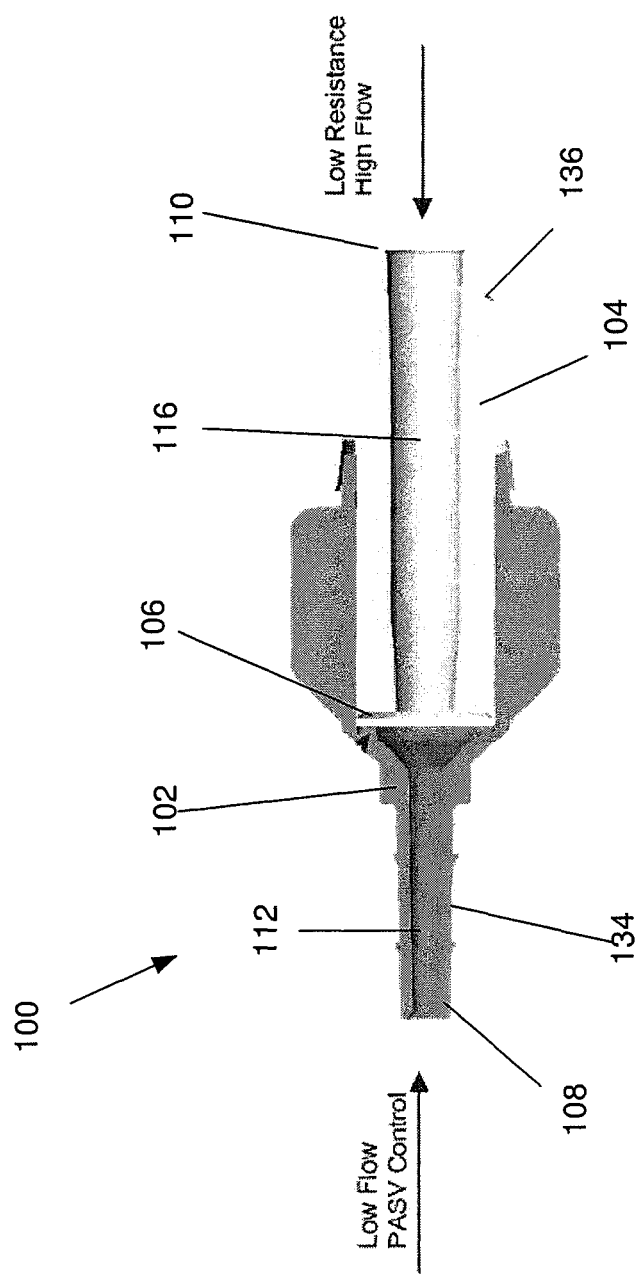
FIG. 1 shows a longitudinal cross-sectional view of a device according to an exemplary embodiment of the present invention.

The present invention may be further understood with reference to the following description and the appended drawings, wherein like elements are referred to with the same reference numerals. The present invention relates to an apparatus for controlling fluid flow through medical devices specifically for sealing devices which remain in place in the body to provide long term access to the vascular system. To improve the performance of pressure activated safety valves, exemplary embodiments of the present invention describe a wedge or other similarly shaped geometrical feature for fixing an elastic component and controlling an internal stress of the elastic component.

Figures 2, 3:
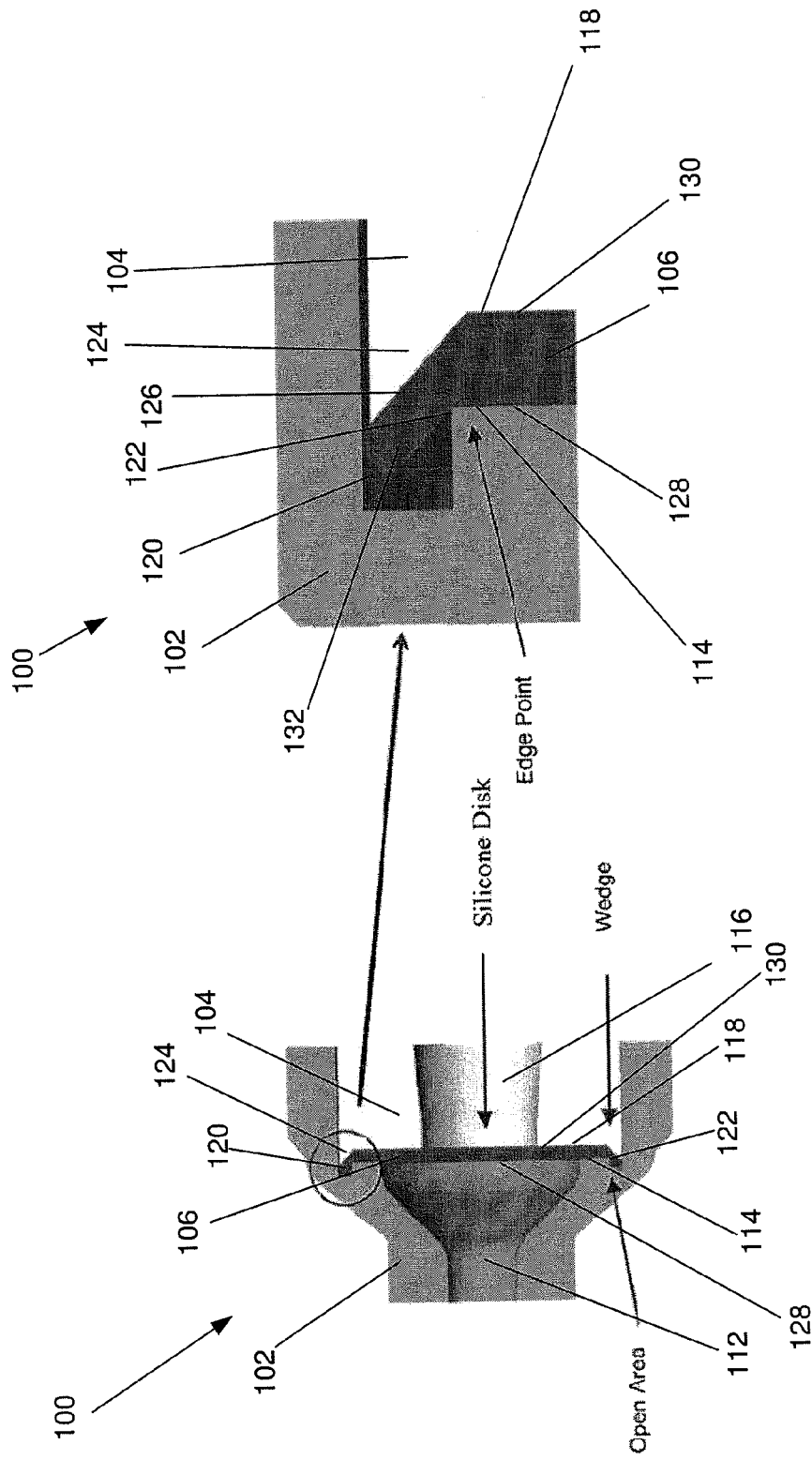
FIG. 2 shows a longitudinal cross-sectional view of a disk portion of the device of FIG. 1.
FIG. 3 shows an enlarged view of portion of an edge of the disk portion of the device shown in FIG. 2.

As shown in FIGS. 1-3, a device 100 according to an exemplary embodiment of the present invention comprises a first housing 102, a second housing 104 and an elastic component 106. As shown in FIG. 1, the first housing 102 and the second housing 104 maybe coupled to one another to fix the elastic component 106 therebetween. For clarity, the elastic component 106 is shown between the first and the second housings 102, 104 before being pinched into the final position. The first housing 102 may form a distal end 108 of the device 100 and includes a first connection 134 for connecting to a first conduit which extends, for example, to a target body structure to and/or from which it is desired to transfer fluids. The second housing 104, at a proximal end 110 of the device 100, includes a second connection 136 for connecting to a second conduit which remains external to the body. The elastic component 106 is fixed between the first and the second housings 102, 104 to control a fluid flow therethrough.

The elastic component 106 may be any flexible membrane (e.g., in the form of a disk) including a slit (not shown) for controlling fluid flow therethrough such as, for example, a silicone disk. The elastic component 106 may operate as a bi-directional valve allowing fluid to flow through the device 100 in either direction whenever the valve is subjected to a fluid pressure of at least a threshold value. Alternatively, the elastic component 106 may operate as a uni-directional valve allowing fluid to flow in only one direction or having different threshold values for each of the two directions of flow therethrough. The elastic component 106 is configured to open only when fluid pressure exerted thereagainst reaches a predetermined threshold magnitude. The slit opens via a deformation of the elastic component 106 with edges of the slit moving away from one another to allow fluid to flow therethrough. Once fluid pressure falls below the threshold magnitude, the slit reseals preventing fluid from flowing therethrough. It will be understood by those of skill in the art that the elastic component 106 may include more than one slit extending therethrough.

As shown in FIGS. 2-3, the first housing 102 includes a lumen 112 extending therethrough and a disk-facing surface 114, which contacts the elastic component 106. The disk-facing surface 114 includes a substantially planar central portion 128 surrounding the lumen 112 and a relief area 120 radially outside the planar central portion 128 (relative to a longitudinal axis of the first and second housings 102, 104). The relief area 120 may be formed as a recess extending around a radially outer edge of the disk-facing surface 114 for accommodating an outer perimeter 132 of the elastic component 106. The relief area 120 further includes an edge 122 over which the outer perimeter 132 of the elastic component 106 may be bent. It will be understood by those of skill in the art that the relief area 120 may be formed as either a continuous recess about the perimeter of the disk-facing surface 114 or as a series of recesses spaced from one another around the circumference of the disk-facing surface 114. In a preferred embodiment, the relief area 120 forms a ring-shaped recess about a circumference of the disk-facing surface 114.

The second housing 104 includes a lumen 116 extending therethrough and a disk-facing surface 118, which contacts the elastic component 106. The disk-facing surface 118 includes a substantially planar central portion 130 surrounding the lumen 116 and a protrusion 124 surrounding the planar central portion 130. The protrusion 124 extends distally away from the planar central portion 130 around a radially outer edge of the disk-facing surface 118. The protrusion 124 may be, for example, wedge-shaped including an angled surface 126 which contacts a radially outer portion of the elastic component 106 bending it over the edge 122 distally into the relief area 120. It will be understood by those of skill in the art that the protrusion 124 may extend continuously about the outer perimeter of the disk-facing surface 118 or may be formed as a series of protrusions separated from one another circumferentially about the outer perimeter of the disk-facing surface 118 by a series of recesses or gaps. In a preferred embodiment, the protrusion 124 is substantially ring-shaped and extends continuously around a circumference of the disk-facing surface 118.

The relief area 120 and the protrusion 124 of the first and the second housings 102, 104, respectively, enhance retention of the elastic component 106 applying compression to the elastic component 106 radially inward toward the longitudinal axis of the first and second housings 102, 104, respectively, to counteract tension to which the elastic component 106 is subjected as it is pinched between the first and second housings 102, 104 and stretched into the relief area 120. Initially, as the elastic component 106 is being pinched between the first and second housings 102, 104, as the outer edge of the elastic component 106 is bent around the edge 122 into the relief area 120, the central portion of the elastic component 106 is stretched radially outward drawing edges of the slit away from one another and puckering the central portion of the elastic component. Then, as the first and second housings 102, 104 are moved further toward one another, the elastic component 106 is pinched between the protrusion 124 and the edge 122 reducing a thickness of this portion of the elastic component 106 and urging the material pinched away from this area toward the slit—i.e., compressing the elastic component 106 radially to bring the edges of the slit back together sealing the valve. The planar portion 130 of the disk-facing surface 118 keeps the central portion of the elastic component 106 substantially flat so that the elastic component 106 does not pucker, aligning edges of the slit while under compression. In addition, the bending of the peripherally outer portion of the elastic component 106 over the edge 122 into the relief area 120 reduces the likelihood that the elastic component 106 will be pulled out of position between the first and second housings 102, 104 when subjected to excess pressure. That is, the outer perimeter 132 of the elastic component 106 extends radially outward of the edge 122 in the relief area 120 with the outer perimeter 132 acting as an anchor holding the elastic component 106 in place.

It will be understood by those of skill in the art that the compression force for closing the slit may be controlled by altering the angle of the angled surface 126 and a position of the protrusion 124 in relation to the edge 122. In a preferred embodiment, the angled surface 126 may be angled from between approximately 40E to 50E and more preferably, at an angle of approximately 45E. The location of the edge 122 may be determined by the angled surface 126, which is positioned to the periphery of the flexible member 106. Thus, the compression force may be controlled as desired. It will also be understood by those of skill in the art that the amount of compression on the slit and/or the elastic component 106 is one of the factors determining the pressure gradients needed to open and close the slit. Other factors may include, for example, a flexibility, a thickness, and a material of the elastic component 106.

It will be apparent to those skilled in the art that various modifications and variations may be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A device to provide access to the vascular system of a patient, comprising:
   a valve component comprising a flexible membrane having a radially outer portion situated between a first mateable housing portion and a second mateable housing portion, said flexible membrane comprising a slit configured to open under a threshold fluid pressure and an outer edge displaced into a recess by at least one of the first and second mateable housing portions, the recess defined by at least one of the first and second mateable housing portions; and
   a catheter in fluid communication with said valve component.

2. The device of claim 1, wherein at least one of the first and second mateable housing portions includes a compression surface configured to displace the outer edge of the flexible membrane, and the recess is positioned radially outward from the compression surface.

3. The device of claim 1, wherein one of the first and second mateable housing portions includes a protrusion, and the flexible membrane is bent by the protrusion.

4. The device of claim 3, wherein the recess is located opposite the protrusion.

5. The device of claim 1, wherein the first and second mateable housing portions define first and second lumens therethrough, respectively, and the flexible membrane incorporates one or more slits therethrough, the one or more slits being aligned to permit fluid communication between the first and second lumens when open.

6. The device of claim 1, wherein one of the first and second mateable housing portions includes a first surface angled relative to a plane defined by the flexible membrane, the first surface being configured to apply radially compressive pressure to the flexible membrane when the flexible membrane is compressed between the first and second housings.

7. The device of claim 6, wherein the recess is located opposite the first surface.

8. A device to provide access to the vascular system of a patient, comprising:
   a valve component comprising a flexible membrane having a radially outer portion situated between a first mateable housing portion and a second mateable housing portion, said flexible membrane comprising a slit configured to open under a threshold fluid pressure and an outer edge displaced into a recess by a protrusion of the first mateable housing portion, the recess defined by the second mateable housing portion; and a catheter in fluid communication with said valve component.

9. The device of claim 8, wherein the recess is defined by the second housing and located opposite the protrusion.

10. The device of claim 8, wherein the protrusion has a surface angled relative to a plane defined by the flexible membrane, the surface being configured to apply radially compressive pressure to the flexible membrane when the flexible membrane is compressed between the first and second housings.

11. The device of claim 8, wherein the first and second mateable housing portions define first and second lumens therethrough, respectively, and the flexible membrane incorporates at least one slit therethrough, the at least one slit being aligned to permit fluid communication between the first and second lumens when open.

* * * * *